United States Patent
Foley et al.

(10) Patent No.: US 6,576,017 B2
(45) Date of Patent: Jun. 10, 2003

(54) SPINAL IMPLANT WITH ATTACHED LIGAMENT AND METHODS

(75) Inventors: Kevin T. Foley, Germantown, TN (US); T. Andrew Simonton, Memphis, TN (US); Craig M. Squires, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/777,797

(22) Filed: Feb. 6, 2001

(65) Prior Publication Data

US 2002/0107572 A1 Aug. 8, 2002

(51) Int. Cl.$^7$ .................................................. A61F 2/44
(52) U.S. Cl. .................................................. 623/17.16
(58) Field of Search .............................. 606/61, 69, 71, 606/70; 623/17.16, 17.15, 17.11; 24/155

(56) References Cited

U.S. PATENT DOCUMENTS

| | | | |
|---|---|---|---|
| 4,599,086 A | * | 7/1986 | Doty ........................ 623/17.11 |
| 4,627,853 A | | 12/1986 | Campbell et al. |
| 4,892,545 A | | 1/1990 | Day et al. |
| 4,946,378 A | | 8/1990 | Hirayama et al. |
| 5,011,484 A | | 4/1991 | Breard |
| 5,053,049 A | | 10/1991 | Campbell |
| 5,092,866 A | | 3/1992 | Breard et al. |
| 5,092,887 A | | 3/1992 | Gendler |
| 5,180,393 A | | 1/1993 | Commarmond |
| 5,423,816 A | * | 6/1995 | Lin ............................. 606/61 |
| 5,458,641 A | | 10/1995 | Ramirez Jimenez |
| 5,562,738 A | | 10/1996 | Boyd et al. |
| 5,591,235 A | | 1/1997 | Kuslich |
| 5,609,634 A | | 3/1997 | Voydeville |
| 5,674,296 A | | 10/1997 | Bryan et al. |
| 5,681,310 A | * | 10/1997 | Yuan et al. .................... 606/61 |
| 5,713,899 A | | 2/1998 | Marnay et al. |
| 5,725,582 A | | 3/1998 | Bevan et al. |
| 5,899,939 A | | 5/1999 | Boyce et al. |
| 5,916,267 A | | 6/1999 | Tienboon |
| 5,989,289 A | | 11/1999 | Coates et al. |
| 6,001,130 A | | 12/1999 | Bryan et al. |
| 6,066,175 A | | 5/2000 | Henderson et al. |
| 6,090,998 A | | 7/2000 | Grooms et al. |
| 6,093,205 A | | 7/2000 | McLeod et al. |
| 6,096,081 A | | 8/2000 | Grivas et al. |
| 6,106,527 A | | 8/2000 | Wu et al. |
| 6,120,503 A | * | 9/2000 | Michelson ..................... 606/61 |
| 6,136,001 A | | 10/2000 | Michelson |
| 6,156,037 A | * | 12/2000 | LeHuec et al. ................ 606/61 |
| 6,190,388 B1 | * | 2/2001 | Michelson et al. ........... 606/61 |
| 6,206,882 B1 | * | 3/2001 | Cohen ........................ 606/69 |
| 6,206,922 B1 | * | 3/2001 | Zdeblick et al. ........ 623/17.11 |
| 6,235,059 B1 | * | 5/2001 | Benezech et al. ....... 623/17.11 |
| 6,306,170 B2 | * | 10/2001 | Ray ........................ 623/17.11 |
| 6,325,827 B1 | * | 12/2001 | Lin .......................... 623/17.16 |

FOREIGN PATENT DOCUMENTS

| | | |
|---|---|---|
| DE | 43 02 397 A1 | 7/1993 |
| WO | WO 97/14377 | 4/1997 |
| WO | WO 97/37620 | 10/1997 |
| WO | WO 99/09914 | 3/1999 |
| WO | WO 99/21515 | 5/1999 |
| WO | WO 99/38453 | 8/1999 |
| WO | WO 99/38463 | 8/1999 |
| WO | WO 01/06933 | 2/2000 |
| WO | WO/0040179 | 7/2000 |
| WO | WO 00/54821 | 9/2000 |

* cited by examiner

Primary Examiner—Eduardo C. Robert
(74) Attorney, Agent, or Firm—Woodard, Emhardt, Moriarty, McNett & Henry LLP

(57) ABSTRACT

Implantable devices are provided useful for creating fusion particularly in intervetebral spinal fusion. The device is formed of any rigid biocompatible material and has a body portion with an attached ligament extending from the body portion. The ligament can extend upwardly from the body portion and downwardly from the body portion, and is made from a flexible material. In one application, the body portion is inserted into a disc space and the flexible ligament is secured to vertebrae on either side of the disc space.

26 Claims, 2 Drawing Sheets

SPINAL IMPLANT WITH ATTACHED LIGAMENT AND METHODS

BACKGROUND OF THE INVENTION

The present invention relates to implantable spinal devices and methods for their use. More particularly, the present invention relates to rigid interbody devices having an attached ligament.

A variety of interbody implants are available for disc replacement and spinal fusion procedures. These implants have been manufactured of various materials including stainless steel, titanium, composites, allograft, xenograft or other biocompatible materials, and have the necessary strength to prevent the disc space from collapsing. Some types of implants have been developed from bio-compatible materials and incorporate threads on the outer surface of the implant that retain the implant in the disc space after it is threaded therein. Still other implants have been developed that are provided with vertebral engaging surfaces on the upper and lower faces of the implant to resist migration of the implant in the disc space and/or expulsion of the implant from the disc space. Other techniques include the placement of one or more interbody fusion devices in the disc space along with a plate or rigid construct that spans the affected disc space. These rigid constructs can be used to apply a compressive load to the inserted implants to further promote fusion.

One disadvantage with some prior art implants is that the implants or other material placed in the disc space might move or migrate in the disc space, creating a risk of expulsion from the disc space and collapse of the disc space. While threaded implants and implants with vertebral engaging surfaces can provide improved migration resistant capabilities, insertion of these implants into the disc space can be difficult and time-consuming, and the migration resistant capabilities of such implants can be improved.

Other techniques contemplate insertion of one or more implants from an anterior approach to the disc space. This approach can require excision of the anterior longitudinal ligament extending across the disc space. When this ligament is removed, the affected spinal joint could be overextended, resulting in expulsion of the one or more implants from the disc space.

There are also disadvantages with prior art spinal fusion techniques that include insertion of an implant in the disc space and placement of a rigid construct across the subject vertebral level to maintain stability of the segment until fusion has been achieved. One disadvantage is that the installation of these constructs can be time consuming and difficult. Further, the rigid construct is permanently implanted into the body, and inhibits flexure of the joint across which the construct is placed. These rigid constructs can also support too much of the spinal column load, resulting in poor incorporation of the implant.

Therefore, there remains a need for improved spinal implants for applications that require both bearing or compression load carrying capabilities to support the spinal column along with capabilities to resist expulsion of the implant from the disc space.

SUMMARY OF THE INVENTION

The present invention is directed to a fusion implant having a rigid portion for insertion between adjacent bony structures and a flexible portion for securement to the adjacent bony structures.

According to one aspect of the invention, there is provided a fusion implant that has a body portion positionable in the disc space between adjacent upper and lower vertebrae. The implant further includes a flexible ligament extending from the body portion along the upper vertebral body and the lower vertebral body.

According to a further aspect of the invention, there is provided a spinal fusion implant that is adapted for insertion into the space between adjacent first and second vertebral bodies. The implant includes a body portion having a first bearing surface for contacting an endplate of the first vertebral body and a second bearing surface for contacting the endplate of the second vertebral body. At least one flexible ligament extends from the body portion so that it can be secured to the first and second vertebral bodies outside the disc space.

According to another aspect of the invention, there is provided a method of inserting an interbody fusion implant. The method includes providing an implant having a rigid body portion with an upper bearing surface and opposite lower bearing surface; accessing the disc space between adjacent vertebrae; inserting the body portion of the implant into the disc space; securing a flexible ligament to the body portion; and securing the flexible ligament to the adjacent vertebrae.

According to a further aspect of the invention, a method of preparing a spinal implant is provided. The method includes obtaining a rigid body portion and attaching a flexible ligament to the rigid body portion. Threads or other bone engaging surfaces can be formed on the body portion.

These and other aspects, advantages, features, embodiments, and objects of the present invention will be apparent to those skilled in the art based on the following descriptions of the illustrated embodiments of the present invention.

DESCRIPTION OF THE ILLUSTRATED EMBODIMENTS

Figure 1:
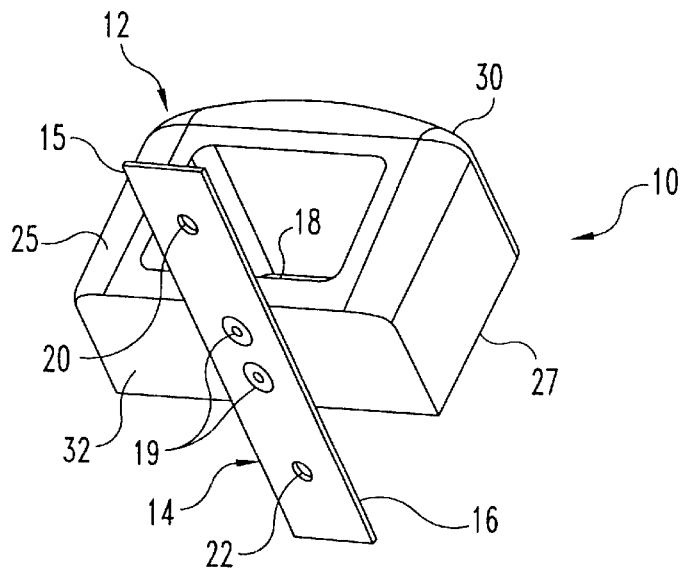
FIG. 1 is perspective view of an implant according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

Referring to FIG. 1, there is shown an implant according to one embodiment of the present invention. Although the rigid implants according to the present invention may have many uses, such as interbody fusion devices or vertebral replacement bodies, the embodiment shown in FIG. 1 is particularly adapted for promoting interbody fusion in the spine. Specifically, FIG. 1 illustrates a spinal implant 10 having a rigid body portion 12 that extends between a leading end 30 and a trailing end 32, and has a height H adapted for insertion into the disc space between adjacent vertebrae. Body portion 12 can be made from any bio-compatible material known to those skilled in the art. Some examples include titanium, composite materials, including carbon composites, surgical stainless steel, to name a few, so long as the material provides body portion 12 sufficient structural integrity to support the spinal column load at the disc space where it is inserted. In one specific application, body portion 12 is a fusion device that provides for fusion between the adjacent vertebrae.

Implant 10 further includes at trailing end 32 a flexible ligament 14 that extends from body portion 12 in the superior and inferior directions. Body portion 12 and flexible ligament 14 can be made as separable components that are secured to one another by fasteners 19. Flexible ligament 14 can be made from any flexible, bio-compatible material, such as an elastomer, demineralized bone, or flexible composite material, to name a few. In one specific form, fasteners 19 are threaded screws that are threaded directly into ligament 14 or through an opening provided in ligament 14 and into a threaded bore formed in body portion 12. The present invention contemplates other techniques for securing the ligament to the body portion, including, for example, riveting, bonding, gluing, welding, fusing, sewing, suturing or interfitting the ligament to the body portion. It is further contemplated that body portion 12 and ligament 14 can be molded as a single unit. In this form, the segments of the molded material forming at least the portions of ligament 14 extending from body portion 12 are flexible. For example, body portion 12 can be molded with a rigid form of composite carbon material and ligament 14 can be formed with body portion 12 from a flexible form of composite carbon material.

Figure 2:
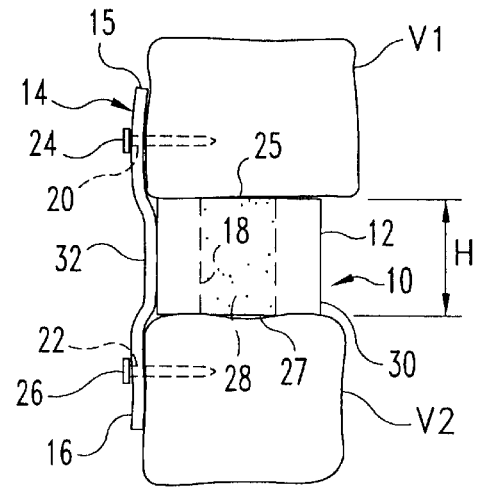
FIG. 2 is a side elevational view of the implant of FIG. 1 inserted in the disc space between adjacent vertebrae.

Referring further to FIG. 2, flexible ligament 14 is secured to body portion 12 between the endplates of the adjacent vertebrae. Ligament 14 has an upper ligament portion 15 that extends in the superior direction along at least a portion of upper vertebral body V1. Flexible ligament 14 also includes a lower ligament portion 16 that extends in the inferior direction along at least a portion of the height of lower vertebral body V2. It is also contemplated that upper portion 15 can extend superiorly to the vertebral body positioned above vertebral body V1, and that lower portion 16 can extend inferiorly to the vertebral body positioned below vertebral body V2. Although upper portion 15 and lower portion 16 are illustrated as having a rectangular shape, other shapes for ligament 14 are also contemplated, such as triangular, square, circular, and other multi-sided and curved shapes. Upper portion 15 can have a first fastener bore 20 for receiving a first fastener 24 and lower portion 16 can have a second fastener bore 22 for receiving a second fastener 26. The fasteners of the present invention can be in the form of a threaded screw and made from metal, bone, polymer, bio-absorbable or resorbable material, or other material known in the art.

The flexibility of ligament 14 permits upper portion 15 and lower portion 16 to be movable with respect to body portion 12 and with respect to each other. Thus, ligament 14 can supplement any remaining portion of the anterior longitudinal ligament or replace the portion of the anterior longitudinal ligament that has been removed to accommodate insertion of body portion 12 into the disc space between vertebral bodies V1 and V2.

Body portion 12 has a cavity 18 to provide an area to receive material that promotes bony incorporation and fusion. Prior to positioning body portion 12 into the disc space, bone growth promoting material 28 may be positioned in cavity 18 to encourage bone growth into and through body portion 12. Bone growth material can be any type of material known in the art. It is further contemplated that body portion 12 can be provided without a cavity for procedures in which spinal fusion is not desired.

Body portion 12 has upper bearing surface 25 that contacts and supports upper vertebral body V1 and lower bearing surface 27 that contacts and supports body portion 12 on lower vertebral body V2. Body portion 12 has height H between upper bearing surface 25 and lower bearing surface 27 that is substantially equal to the height of disc space formed between vertebra V1 and vertebra V2. Body portion 12 has a uniform height H as shown in FIG. 2, it will be understood that the implants of the present invention may have a tapering height such that the implant could be utilized for establishing or maintaining the proper angulation between the endplates. Fasteners 24 and 26 are placed through the corresponding fastener bores 20 and 22 in the upper and lower portions 15 and 16, respectively, to stabilize body portion 12 in the disc space. Since ligament 14 is flexible, it can be manipulated and positioned adjacent the vertebral bodies outside the disc space without the creation of large shear and bending stresses in body portion 12.

Vertebrae V1 and V2 are accessed from an anterior approach using known surgical techniques. The disc material is removed and the disc space height is restored, if necessary, using known surgical techniques. Body portion 12 is inserted into the prepared disc space and upper portion 15 is attached to V1 and lower portion 16 is attached to V2. Body portion 12 is adapted to provide structural support between the respective lower bearing surface of upper vertebra V1 and lower bearing surface of vertebra V2. In the illustrated embodiment, rigid body portion 12 has a height H sufficient to provide support for and maintain the desired spacing between adjacent vertebra V1 and V2. If desired, fusion between vertebrae V1 and V2 is obtained with bone growth through cavity 18, which is filled with bone growth material 28. Fusion between the vertebrae can be further promoted by reducing the endplates to bleeding bone prior to insertion of body portion 12.

In one specific application, implant 10 is positioned from an anterior approach is for fusion of the cervical spine. Body portion 12 can have any shape, including a specific shape for insertion in the disc space in the cervical region, such as those shapes and configurations identified in U.S. Pat. No. 5,989,289 which is incorporated herein by reference in its entirety. In another specific application, implant 10 is positioned from an anterior approach to the lumbar spine. In these applications, body portion 12 can have a shape adapted for insertion in the disc space in the lumbar region of the spine, such as those shapes and configurations shown in U.S. Pat. Nos. 5,984,967 and 5,397,264, each of which is incorporated herein by reference in its entirety.

In one surgical technique, a tensile force can be applied to upper portion 15 prior to insertion of fastener 24. When fastener 24 is secured to vertebra V1, the tensile force is released. Fastener 26 can be similarly inserted through bore 22 of a tensioned lower portion 16. The pre-tensioned ligament 14 thus applies a compressive load on body portion 12 in the disc space with vertebrae V1 and V2, further promoting fusion and incorporation of body portion 12, if desired, and inhibiting expulsion of body portion 12 from the disc space.

Figure 3:
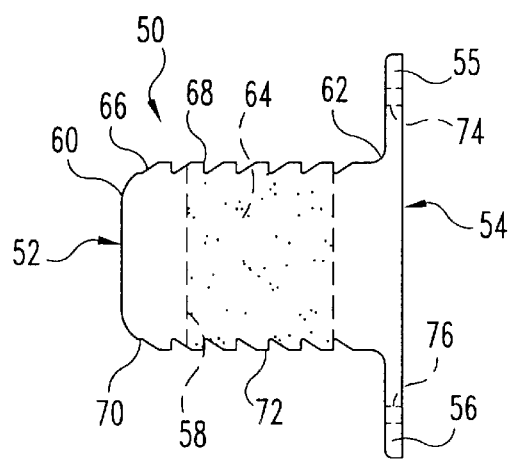
FIG. 3 is a side elevational view of another embodiment implant according to the present invention.

Referring now to FIG. 3, a further embodiment implant is shown and designated at 50. Implant 50 is similar to implant 10. Implant 50 includes rigid body portion 52 extending between a leading end 60 and a trailing end 62. Implant 50 further includes a flexible ligament 54 extending from trailing end 62. Ligament 54 includes an upper portion 55 and a lower portion 56. A first fastener bore 74 is formed through upper portion 55 and a second fastener bore 76 is formed through lower portion 56. Body portion 52 includes a cavity 58 in which bone growth material 64 can be placed.

Body portion 52 further includes a number of upper bone engagement ridges 68 formed on and extending upwardly from an upper bearing surface 66, and a number of identical lower ridges 72 formed on and extending downwardly from a lower bearing surface 70. It will be understood that while ridges have been shown in the illustrated embodiment, it is contemplated that there are a variety of structures which could provide a surface for effective engagement with the vertebral bodies to limit expulsion from the disc space. Examples of some such further structures are discussed in U.S. Pat. No. 5,989,289. Further, the endplates or bearing surfaces of the adjacent bony structure can be roughened or otherwise shaped to retain the body portion 52 in its inserted position.

Figure 4:
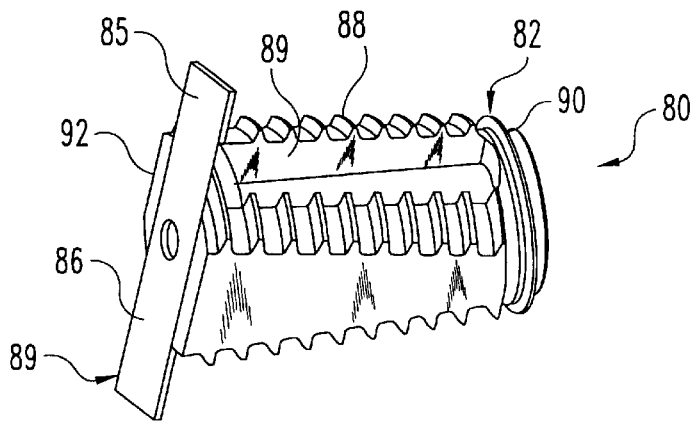
FIG. 4 is a perspective view of yet another embodiment implant according to the present invention.

Referring now to FIG. 4, there is shown another embodiment implant 80 for use in vertebral fusion procedures having particular application in the lumbar region of the spine. Implant 80 has a rigid body portion 82 extending between a leading end 90 and a trailing end 92. A number of threads 88 can be formed on the exterior of body portion 82 and are provided to engage the vertebral endplates, although a non-threaded body portion 82 is also contemplated. Body portion 82 can have a cavity (not shown) for placement of bone growth material and one or more openings 89 formed through body portion 82 communicating with the hollow interior. Body portion 82 includes an upper bearing surface 94 and a lower bearing surface 95. The distance between these bearing surfaces 94, 95 of body portion 82 are tapered from a reduced height H1 at leading end 90 to a greater height H2 at trailing end 92. A flexible ligament 84, similar to ligament 14 described above, is attached to body portion 82 between the upper and lower bearing surfaces 94, 95 at trailing end 92. Ligament 84 includes an upper portion 85 and a lower portion 86 extending from body portion 82.

Figure 5:
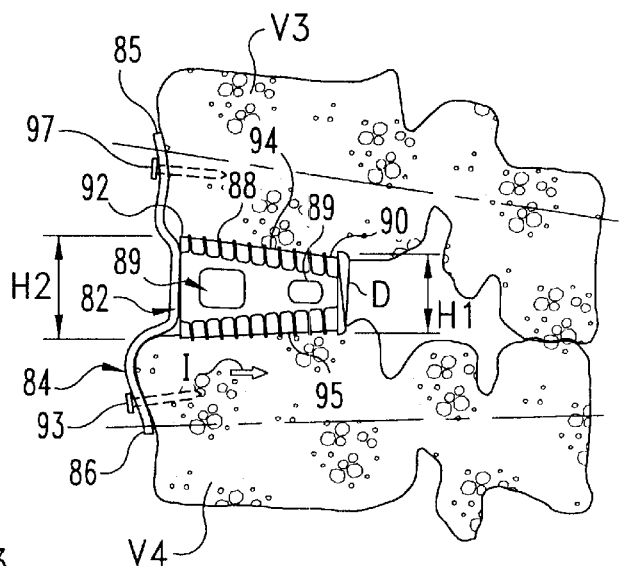
FIG. 5 is a side elevational view of the implant of FIG. 4 inserted in the disc space between adjacent vertebrae.

Body portion 82 is positioned in disc space D as shown in FIG. 5 using known surgical techniques to prepare the disc space and vertebral endplates. Such techniques can include removing disc space material, and reaming and tapping the vertebral endplates to receive body portion 82, if necessary. When body portion 82 is positioned between the adjacent vertebrae, upper portion 85 and lower portion 86 of ligament 84 are positioned adjacent the vertebral bodies V3 and V4, respectively, outside the disc space. Once body portion 82 is secured in the disc space D, fasteners 97 and 98 can be used to secure the upper and lower portions of ligament 84 to the respective adjacent vertebral body. In one form, it is contemplated that ligament 84 is attached to body portion 82 after body portion 82 is positioned in disc space D. In another form, it is contemplated that ligament 84 can be attached to body portion 82 during insertion into disc space D, and that ligament 84 provides access to implant driving tool engagement means at trailing end 92.

Figure 6:
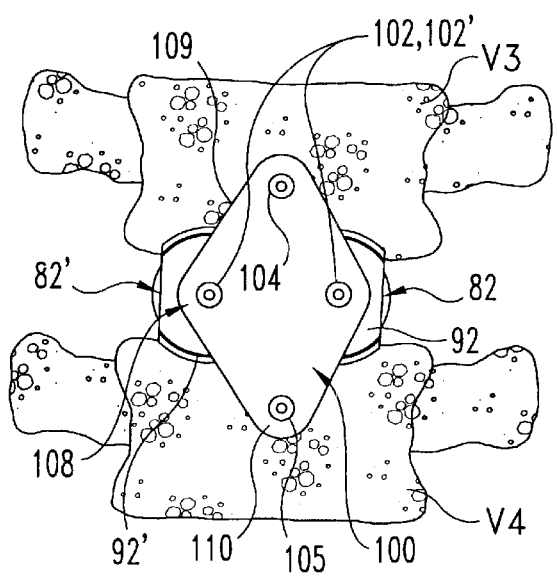
FIG. 6 is an end elevational view of a pair of the implants of FIG. 4 inserted in side-by-side relation in the disc space between adjacent vertebrae.

As shown in FIG. 6, it will be understood that a second body portion 82' can be placed in disc space D adjacent the first inserted body portion 82 to provide further stability to the spinal column. A flexible ligament 100 is attachable to body portions 82, 82' via fasteners 102 and 102'. Flexible ligament 100 has a widened mid-portion 108 sized to extend between the adjacent body portions 82, 82'. In one form, ligament 100 includes an upper portion 109 having a tapered width forming an inverted V-shape that extends upwardly from mid-portion 108. Ligament 100 also includes a lower portion 110 having a tapered width forming a V-shape that extends downwardly from mid-portion 108. Other shapes for ligament 100 are also contemplated, such as rectangular, square, circular, and other multi-sided shapes. Fasteners 104, 105 secure the ligament to vertebral bodies V3 and V4.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal system, comprising:
   a first implant including:
   a first body portion positionable in a disc space between adjacent upper and lower vertebrae;
   a second implant including:
   a second body portion positionable in the disc space between adjacent upper and lower vertebrae; and
   a flexible ligament extending from each of said first body portion and said second body portion and positionable along the upper vertebra and along the lower vertebra when said first body portion and said second body portion are positioned in the disc space, wherein said flexible ligament is made from a flexible material.

2. The system of claim 1, wherein:
   said first body portion has a leading end and an opposite trailing end, and said flexible ligament is attached to said trailing end of said first body portion; and
   said second body portion has a leading end and an opposite trailing end, and said flexible ligament is attached to said trailing end of said second body portion.

3. The system of claim 2, wherein each of said first and second body portions includes an upper bearing surface and a lower bearing surface separated by a height, said height adapted to maintain spacing between the adjacent vertebrae.

4. The system of claim 3, wherein said height is tapered and increases from said leading end to said trailing end of said first and second body portions.

5. The system of claim 3, wherein each of said upper and lower bearing surfaces of each of said first and second body portions includes a bone engaging surface to inhibit expulsion of the implant from the disc space.

6. The system of claim 5, wherein each of said first and second body portions is configured for rotatable insertion into the disc space and each of said bone engaging surfaces is threaded.

7. The system of claim 1, wherein said flexible ligament is movable relative to each of said first and second body portions.

8. The system of claim 1, wherein at least one of said first and second body portions is shaped for push-in insertion in the disc space.

9. The system of claim 1, wherein said first and second implants are spinal fusion devices.

10. The system of claim 1, wherein said flexible ligament includes:

a first opening formed therethrough to receive a first fastener to secure the ligament the upper vertebra; and a second opening formed therethrough to receive a second fastener to secure the ligament the lower vertebra.

11. The system of claim 1, wherein said flexible ligament is removably attachable to at least one of said first and second body portions.

12. The system of claim 1, wherein at least one of said first and second body portions includes a cavity allowing bone growth between the upper and lower vertebrae.

13. The system of claim 1, wherein said artificial ligament has an upper portion extending along the upper vertebra and a lower portion extending along the lower vertebra, said upper portion and said lower portion each being movable relative to another and movable relative to said first and second body portions.

14. A method of fusing adjacent vertebrae through a disc space between adjacent vertebrae, comprising:

providing a hollow implant having a body portion with an upper bearing surface and opposite lower bearing surface, the implant further including a flexible ligament securable to the body portion;

placing bone growth material in the hollow implant;

accessing the disc space between adjacent vertebrae;

inserting the body portion of the implant into the disc space;

providing a second implant having a body portion with an upper bearing surface and opposite lower bearing surface;

inserting the body portion of the second implant into the disc space;

securing the flexible ligament to the body portion of the hollow implant and the body portion of the second implant; and securing the flexible ligament to one of the adjacent vertebrae.

15. The method of claim 14, further comprising securing the flexible ligament to the other of the adjacent vertebrae.

16. The method of claim 15, wherein:

securing the flexible ligament includes engaging a fastener to each of the adjacent vertebrae through a corresponding opening formed through the flexible ligament.

17. The method of claim 14, wherein accessing the disc space includes accessing the disc space via an anterior approach.

18. The method of claim 14, wherein accessing the disc space includes accessing the disc space between adjacent lumbar vertebrae.

19. The method of claim 14, further comprising attaching the flexible ligament to the body portion at a location between the adjacent vertebrae after inserting the body portion into the disc space.

20. A method of preparing a spinal implant, comprising:

providing a first body portion and a second body portion adapted for insertion in a spinal disc space between adjacent first and second vertebrae;

providing bone engaging surfaces on the first and second body portions;

inserting the first and second and body portions in the spinal disc space; and attaching a flexible ligament to the first and second body portions, said flexible ligament including a first portion extending from the first and second body portions in a first direction for attachment to the first vertebra and a second portion extending from the first and second body portions in a second direction for attachment to the second vertebra.

21. The method of claim 20, further including providing the first and second body portions with a hollow interior and placing bone growth material therein.

22. The method of claim 20, further comprising securing the flexible ligament to the first and second vertebrae.

23. The method of claim 22, wherein:

securing the flexible ligament to the first and second vertebrae includes engaging a fastener to each of the first and second vertebrae through a corresponding opening formed through the flexible ligament.

24. The method of claim 20, further comprising accessing the spinal disc space via an anterior approach.

25. The method of claim 20, further comprising accessing the spinal disc space between adjacent lumbar vertebrae.

26. The method of claim 20, further comprising attaching the flexible ligament to the first and second body portions after inserting the first and second body portions into the spinal disc space.

* * * * *